United States Patent
Marty et al.

(10) Patent No.: US 7,129,206 B2
(45) Date of Patent: Oct. 31, 2006

(54) UTILIZATION OF UNSATURATED ESTERS AS PERFUMING INGREDIENTS

(75) Inventors: Maurus Marty, Morristown, NJ (US); Christian Vial, Geneva (CH)

(73) Assignee: Firmenich SA, Geneva (CH)

( * ) Notice: Subject to any disclaimer, the term of this patent is extended or adjusted under 35 U.S.C. 154(b) by 288 days.

(21) Appl. No.: 10/341,452

(22) Filed: Jan. 14, 2003

(65) Prior Publication Data

US 2003/0144173 A1    Jul. 31, 2003

(30) Foreign Application Priority Data

Jan. 18, 2002  (WO) ....................... PCT/IB02/00157

(51) Int. Cl.
*A61Q 13/00*    (2006.01)
(52) U.S. Cl. ............... 512/25; 512/26; 512/27; 560/8
(58) Field of Classification Search ............ 512/25–27; 560/8
See application file for complete search history.

(56) References Cited

U.S. PATENT DOCUMENTS

| | | | |
|---|---|---|---|
| 3,066,120 A | 11/1962 | Snelgrove | 260/89.1 |
| 3,878,074 A | 4/1975 | Reichenbacher et al. | 204/158 |
| 3,936,473 A | 2/1976 | Symon et al. | 260/343.2 |
| 6,602,535 B1 * | 8/2003 | Farbood et al. | 426/534 |

OTHER PUBLICATIONS

T. Watanabe, et al., XP-002268178, "Acylation Of Beta-OxoalKyltetracarbonylferrate(0). A Novel Route To Enol Ester", Elsevier science Publisher, Tetrahedron Letters., No. 36,, pp. 3163-3164 (1975).

H. M. Jung, et al., XP-002268179, "Concerted Catalytic Reactions For Conversion Of Ketones Or Enol Acetates To Chiral Acetates", American Chemical Society, Organic Letters. vol. 2, No. 3, pp. 409-411 (2000).

J. Harrison, XP002268180 "Dehydration Of Ketones To Acetylenes", American Chemical Society, Journal Of Organic Chemistry., vol. 44, No. 20, pp. 3578-3580, (1979.

J. P. Patel, Ee al., XP008026974 ,"Enol Esters As Potential Pro-Drugs II. In Vitro Aqueous Stability And Enzyme-Mediated Hydrolysis Of Several Enol Esters Of Acetophenone" International Journal Of Pharmaceutics, vol. 9, pp. 29-47,( 1981).

D.S. Noyce et al., XP002268539, "Two Mechanisms For The Acid-Catalyzed Hydrolysis Of Enol Acetates" Technical Fields American Chemical Society, Journal Of The American Chemical Society., vol. 91, No. 1, , pp. 119-124, (1969).

* cited by examiner

*Primary Examiner*—Monique T. Cole
(74) *Attorney, Agent, or Firm*—Winston & Strawn LLP

(57) ABSTRACT

A compound of formula

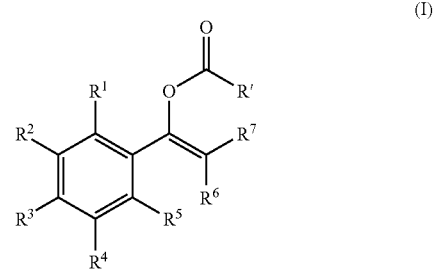

(I)

wherein the symbol R' represents a linear or branched, unsaturated or saturated hydrocarbon group having from 1 to 5 carbon atoms; $R^1$, $R^2$, $R^3$, $R^4$ and $R^5$ represent, independently of each other, a hydrogen atom, a methyl, an ethyl or a methoxy group; $R^6$ and $R^7$ represent, independently of each other, a hydrogen atom, a methyl, ethyl, n-propyl or iso-propyl group; and wherein $R^5$ and $R^6$, when taken together with the carbon atoms to which they are bound, may form a six-membered ring, is useful as perfuming ingredient for the preparation of perfuming compositions and perfumed products, to which it imparts odor notes of the floral and indol type without coloring problems in the final product.

9 Claims, No Drawings

UTILIZATION OF UNSATURATED ESTERS AS PERFUMING INGREDIENTS

BACKGROUND OF THE INVENTION

The present invention relates to the field of perfumery. It concerns more particularly the use as a perfuming ingredient of a compound of formula

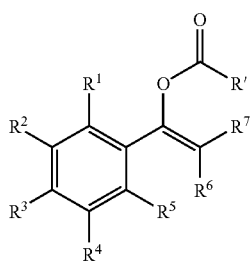

(I)

wherein symbol R' represents a linear or branched, unsaturated or saturated hydrocarbon group having from 1 to 5 carbon atoms; $R^1$, $R^2$, $R^3$, $R^4$ and $R^5$ represent, independently of each other, a hydrogen atom, a methyl, an ethyl or a methoxy group; $R^6$ and $R^7$ represent, independently of each other, a hydrogen atom, a methyl, ethyl, n-propyl or iso-propyl group; and wherein $R^5$ and $R^6$, when taken together with the carbon atoms to which they are bound, may form a six-membered ring.

The esters of formula (I) possess very useful and appreciated odor properties. Therefore, they can be used for the preparation of perfumes, perfuming compositions and perfumed products. They are employed in particular to confer floral odor notes to the products to which they are added.

Some compounds represented by formula (I) are known. More particularly, the latter are cited as reactants, intermediates or end-products of synthesis in many scientific articles. However, their organoleptic properties have never been outlined in any document from the prior art, and therefore, their potential use in the field of perfumery, in particular as perfuming ingredients, has never been mentioned nor even suggested in the prior art.

SUMMARY OF THE INVENTION

Now, we have been able to establish that the esters defined by formula (I) possess very interesting organoleptic properties. A first object of the present invention is therefore a method of use as a perfuming ingredient of a compound of formula

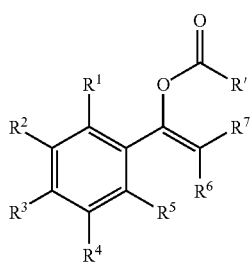

(I)

wherein the symbol R' represents a linear or branched, unsaturated or saturated hydrocarbon group having from 1 to 5 carbon atoms; $R^1$, $R^2$, $R^3$, $R^4$ and $R^5$ represent, independently of each other, a hydrogen atom, a methyl, an ethyl or a methoxy group; $R^6$ and $R^7$ represent, independently of each other, a hydrogen atom, methyl, ethyl, n-propyl or iso-propyl group; and wherein $R^5$ and $R^6$, when taken together with the carbon atoms to which they are bound, may form a six-membered ring.

A further object of the invention concerns perfuming compositions or perfumed products containing a compound of formula (I) as defined above, as active ingredient.

DETAILED DESCRIPTION OF THE INVENTION

In a general manner, the compounds of the invention all present very pleasant floral type odor notes.

The compounds defined by formula (I) can be in particular advantageously used to confer floral and indolic odor notes. In a particular embodiment of the invention, they provide an unexpected and advantageous alternative for perfumers to the use of indole in perfuming compositions and perfumed product. In fact, indole is a widely known perfuming ingredient, especially used to impart floral notes in jasmine, lilac, neroli, gardenia and numerous other heavy or exotic flower type fragrance bases. However, as a result of its chemical structure, indole may cause some problems in perfumery when incorporated in particular in compositions containing aldehydes. In some cases a condensation process leads to a new product with a change in color and viscosity. The change in color is sometimes really important and may be a real problem depending on the application considered for the end product. The sensitivity of indole to daylight is well known to perfumers and the problem of finding an alternative product not presenting the same coloration problem has been discussed for a long time. Some colorless substitutes are known, such as for instance indomethylene (4,4A,5,9B-tetrahydro-indeno[1,2D]-1,3-dioxin), but these ingredients do not have an olfactory strength comparable to that of indole.

Now, the compounds of the invention provide a solution to the problems above-mentioned, as they possess an indolic olfactory note of substantial volume and of a power easily comparable to that of indole. Moreover, the compounds of formula (I) can be admixed with any other perfuming ingredients, solvents or adjuvants of current use in the preparation of perfume formulations, without providing any coloration problem in the final application.

Amongst the compounds of the invention, those of formula (I) wherein $R^1$, $R^2$, $R^3$, $R^4$, $R^5$, $R^6$ and $R^7$ all represent hydrogen atoms are preferred. Amongst the latter, 1-phenylvinyl acetate is particularly appreciated. The odor of the latter can be described as being indolic and also close to that of indomethylene (4,4A,5,9B-tetrahydroindeno[1,2D]-1,3-dioxin). This odor can be described as being floral, with a jasmine connotation and is very appreciated by perfumers for providing a subtle mixture of floral, animal and indolic elegant odor notes. As shown in the examples below, this compound has proved to be clearly superior to other known substitutes of indole. Its odor is in fact more powerful than that of indomethylene, more elegant, more floral and less naphthalenic.

1-Phenylethenyl propanoate is also a well-appreciated compound of the invention. In addition to jasmin and indolic top notes, the odor of the latter present a bitter almond connotation, accompanied by phenolic, aldehydic, green and Sambac jasmin bottom notes.

The compounds of the invention can suit an utilization in fine perfumery, in perfumes, colognes, or after-shave lotions, as well as any current use in functional perfumery such as the perfuming of soaps, shower or bath gels, hygiene products, hair-care products such as shampoos, as well as deodorants and air-fresheners, or yet cosmetic preparations.

The compounds (I) can also be used in applications such as liquid or solid detergents for textile treatment, fabric softeners, or yet detergent compositions or cleaning products for dishes or varied surfaces, for a domestic as well as an industrial use.

In these applications the compounds of the invention can be used alone as well as mixed with other perfuming ingredients, solvents or adjuvants currently used for the preparation of a perfume formulation.

Therefore, a second object of the invention is to provide a perfuming composition or a perfumed product containing as active ingredient, together with other perfuming ingredients, solvents or adjuvants currently used for the preparation of a perfume formulation, a compound of formula (I) such as defined above.

The term "perfuming composition", also often referred to as the simple term "perfume", is widely used in perfumery. It designates, in a general manner, a blend of odoriferous materials, perceived as having its own unique and aesthetically appropriate identity. More particularly, it is a carefully balanced blend based on a definite structure (specific ingredients and specific proportions of each of them) in which each material plays its part in achieving the overall fragrance. This creative and original composition is thus structurally characterised by a formulation constituted by the ingredients themselves and their relative proportions.

Therefore, a perfuming composition in the field of perfumery is not just a mixture of pleasantly smelling materials. On the other hand, it is clearly understood by a skilled person in the art that a chemical reaction involving reactants and products formed, which constitutes a dynamic system, cannot be compared, unless otherwise specified, to perfuming compositions, even when odorants materials are present among the starting products, the formed products, or even both of them.

The perfuming co-ingredients present in such compositions belong to varied chemical groups such as alcohols, aldehydes, ketones, esters, ethers, acetates, nitrites, terpenic hydrocarbons, heterocyclic nitrogen- or sulfur-containing compounds, as well as essential oils of natural or synthetic origin. Many of these ingredients are listed in reference texts such as S. Arctander, Perfume and Flavour Chemicals, 1969, Montclair, N.J., USA or more recent versions thereof, or in other similar books.

Now, apart from having a well defined identity, a perfume or perfuming composition must meet a number of technical requirements. It must for instance be sufficiently strong, it must be diffusive, it must be persistent, and it must retain its essential fragrancing character throughout its period of evaporation. Besides, a perfuming composition must be adapted as a function of the application for which it is intended. In particular, a perfuming composition may be designed for a fine fragrance or designed for functional products, as mentioned below, which require a degree of persistence appropriate to the use to which they are intended. The composition must also be chemically stable in the end product. The technique by which this is achieved is an essential part of the perfumer's art, and it is needed many years of dedicated work to arrive at the level of experience necessary to formulate perfumes or perfume compositions that are not only original but also well made. Now, these technical considerations imply that a perfuming composition may comprise other ingredients than perfuming materials, and which are hereby designated as "solvents or adjuvants of current use in the preparation of a perfume formulation".

First of all, independently of whether the composition is designed for fine perfumery or for use in a technical product, a solvent system is most of the time part of the fragrance. Solvents currently used in the preparation of a perfume formulation are well known by a person skilled in the art and include in particular, dipropylene gylcol, diethyl phtalate, isopropyl myristate, benzyl benzoate, 2-(2-ethoxyethoxy)-1-ethanol or ethyl citrate for the most currently used.

On the other hand, the creation of perfume compositions intended for functional products involve considerations both of aesthetics (how should the product smell) and of the technique of adapting the perfume to the product formulation or, as is often said, to the product base. The perfuming compositions may therefore comprise "adjuvants" which can have many different functions, depending on the base which has to be perfumed. These adjuvants include for instance stabilizers such as antioxidants.

Today, the range of product types and product formulations that are perfumed has become so extensive and subjected to such frequent changes that an approach based on a product-by-product basis and on the definition for each case of the adjuvants that can be used, is impractical. That is why the present application does not comprise an exhaustive list or detailed approach of the solvents or adjuvants currently used in the formulations of perfume compositions. However, a skilled person in the art, i.e. an expert perfumer, is capable of choosing these ingredients as a function of the product to be perfumed and of the nature of the perfuming ingredients contained in the perfume.

The proportions in which the compounds according to the invention can be incorporated in the different products or compositions mentioned above, vary in a large range of values. These values depend on the nature of the article or product that has to be perfumed, and on the olfactory effect sought, as well as on the nature of the co-ingredients in a given composition when the compounds of the invention are used in admixture with perfuming co-ingredients, solvents or additives of current use in the art.

For instance, typical concentrations from about 4 to 15% by weight, or even 20% or more by weight of the compound (I) of the invention, with respect to the weight of the composition in which it is incorporated can be used. Much lower concentrations than these can be used when these compounds are directly applied for perfuming the consumer products mentioned above.

The compounds of the invention can be prepared by a transesterification reaction, starting from a suitable ketone, chosen as a function of the desired final product, in the presence of an acylating agent to transform the former in the corresponding enol ester. The synthesis will be described in a more detailed manner in the examples below.

The invention will now be described in greater detail in the following examples, wherein the temperatures are indicated in degrees centigrade and the abbreviations have the usual meaning in the art.

EMBODIMENTS OF THE INVENTION

EXAMPLE 1

Preparation of 1-phenylvinyl Acetate

A 2.5 l jacketed cylindrical reactor was charged with 10 g (1% w/w) of para-toluene sulphonic acid (pTSA), 1000.0 g (8.34 mol, 1.0 eq) of acetophenone (origin: Acros) and 166.8 g (1.67 mol, 0.2 eq) of isopropenyl acetate (origin: Wacker). The temperature of the fluid in the jacket was raised to 120°. As soon as the pot temperature reached 115°, 667.3 g of isopropenyl acetate (6.67 mol, 0.8 eq) were introduced over the course of 5 hours while distilling off the acetone formed during the reaction. At the end of introduction, the conversion reached 50%. Stirring was continued for a further 2 hours (conversion 58%). The pot temperature was then decreased to 25°. A total of 250 g distillate were collected (80% acetone, 20% isopropenyl acetate). 19.5 g (0.06 mol, 1.05 eq/pTSA) of trioctylamine were added, and stirring was continued for 1 hour at 25°. The reaction mixture was concentrated at 80° while gradually reducing the pressure from 360 hPa to 40 hPa. A total of 362 g of distillate (75% isopropenyl acetate, 25% acetone) were collected. The crude product (1269 g) was flash distillate (6–0.5 hPa, 73–69°) to yield a first fraction of a mixture of 1-phenylvinyl acetate and acetophenone (685 g; 25:75; 13%) and a second fraction of 1-phenylvinyl acetate (500 g; 97.2% GC; 36%).

Analytical Data:

IR(neat): 3059(w); 1763(s); 1646(m); 1577(w); 1494(m); 1446(m); 1370(s); 1270(m); 1216(s); 1098(m); 1077(m); 1021(s); 960(m); 884(m); 774(s); 710(m).

NMR($^1$H, 360 MHz, CDCl$^3$): 7.47–7.44(m, 2H); 7.36–7.30(m, 3H); 5.47(d, J=2.4, 1H); 5.02(d, J=2.0, 1H); 2.26(s, 3H).

NMR($^{13}$C, 90.5 MHz, CDCl$_3$); 169.1(s); 153.0(s); 134.3(s); 129.0(d); 128.5(d); 124.9(d); 102.1(t); 21.0(q).

MS: 162(12, M$^+$); 134(11); 120(100, M$^+$-ketene); 105(57); 91(21); 78(41); 65(10); 51(19); 43(64).

EXAMPLE 2

Preparation of 1-(3-methylphenyl)ethenyl Acetate

Using a 15 cm Wiedmer distillation apparatus, a solution of 50 mmol of 3-methyl acetophenone in 15.02 g (150 mmol) of isopropenyl acetate was heated at 95° in the presence of 75 mg of para-toluene sulphonic acid. At a stabilised conversion (50–70% by GC, after 8 h at 95°), the mixture was cooled and 300 mg of trioctylamine were added. After extraction by means of ether, and usual workup, the product was distilled on a bulb-to-bulb apparatus and purified by preparative GC using a 1.2 m×6 mm column loaded with 10% SE-30 on Supelcoport® 80–100 mesh, vector gas: helium at 30 ml/min. The product was obtained in 60% yield Analytical Data:

NMR($^1$H, 360 MHz, CDCl$_3$): 2.27(s, 3H); 2.35(s, 3H); 4.99(split s, 1H); 5.45(split s, 1H); 7.1(d: J=8, 1H); 7.24(m, 3H).

NMR($^{13}$C, 90.5 MHz, CDCl$_3$): 21.0(q); 21.5(q); 101.8(t); 122.0(d); 125.5(d); 128.4(d); 129.8(d); 134.2(s); 138.2(s); 153.1(s); 169.1(s).

MS: 176(M$^+$, 22); 134(100); 119(41); 92(47); 43(21).

EXAMPLE 3

Preparation of 1-(2-methylphenyl)ethenyl Acetate 1-(2-Methylphenyl)ethenyl acetate was prepared as described in Example 2, starting from 2-methyl-acetophenone, in 39% yield.

Analytical Data:

NMR($^1$H, 360 MHz, CDCl$_3$): 2.13(s, 3H); 2.41(s, 3H); 5.02(split s, 1H); 5.17(split s, 1H); 7.16(m, 2H); 7.23(m, 1H); 7.37(d: J=7.5, 1H).

NMR($^{13}$C, 90.5 MHz, CDCl$_3$): 20.3(q); 21.0(q); 105.7(t); 125.6(d); 128.8(d); 129.1(d); 130.5(d); 135.4(s); 135.9(s); 153.8(s); 168.8(s).

MS: 176(M$^+$, 12); 134(33); 119(100); 91(22); 43(19).

EXAMPLE 4

Preparation of 1-(4-ethylphenyl)vinyl Acetate 1-(4-Ethylphenyl)vinyl acetate was prepared as described in Example 2, starting from 4-ethyl-acetophenone, in 49% yield.

Analytical Data:

NMR($^1$H, 360 MHz, CDCl$_3$): 1.22(t: J=8, 3H); 2.27(s, 3H); 2.64(q: J=8, 2H); 4.96(split d, 1H); 4.53(split d, 1H); 7.17(d: J=9, 2H); 7.38(d: J=9, 2H).

NMR($^{13}$C, 90.5 MHz, CDCl$_3$): 15.4(q); 21.0(q); 28.6(t); 101.3(t); 124.9(d, 2C); 128.1(d, 2C); 131.7(s); 145.3(s); 153.1(s); 153.8(s); 169.1(s).

MS: 190(M$^+$, 17); 148(100); 133(86); 91(12); 43(13).

EXAMPLE 5

Preparation of 1-(4-methoxyphenyl)ethenyl Acetate 1-(4-Methoxyphenyl)ethenyl acetate was prepared as described in Example 2, starting from 4-methoxy-acetophenone, in 36% yield. This compound was purified by chromatography (SiO2, pentane/ether 6/4) and crystallisation (heptane/ether 6/1).

Analytical Data:

Mp=78.5–80°

NMR($^1$H, 360 MHz, CDCl$_3$): 2.26(s, 3H); 3.80(s, 3H); 4.91(split s, H); 5.35(split s, 1H); 6.86(split d: J=9, 2H); 7.39(split d: J=9, 2H).

NMR($^{13}$C, 90.5 MHz, CDCl$_3$): 21.0(q); 55.3(q); 100.2(t); 113.9(d, 2C); 126.3(d, 2C) 126.9(s); 152.7(s); 160.2(s); 169.1(s).

MS: 192(M$^+$, 25); 150(100); 135(73); 108(9); 92(5); 77(11); 43(13).

EXAMPLE 6

Preparation of 1-phenylethenyl Propanoate

A solution of 8.11 g (50 mmol) of 1-phenylvinyl acetate (prepared as described in Example 1) in 80 ml of anhydrous tetrahydrofuran was placed in a 500 ml round bottomed flask and cooled to −75°. A solution of 6.16 g (55 mmol) of potassium tert-butylate in 60 ml of anhydrous tetrahydrofuran was slowly added (40') and the mixture was stirred for 1 h at −75°. A solution of propionyl chloride (55 mmol) in 20 ml of anhydrous tetrahydrofuran was slowly added (20') and, after 2 h at −75°, the cooling bath was removed and 60 ml of a saturated solution of NaHCO$_3$ was rapidly added. The temperature rose rapidly to −10° and the mixture was extracted with ether. After usual workup, the product was purified by flash chromatography (SiO$_2$, pentane/ether 8/2), bulb-to-bulb distillation and preparative GC using a 1.2 m×6 mm column loaded with 10% SE-30 on Supelcoport® 80–100 mesh, vector gas: helium at 30 ml/min. The product was obtained in 14% yield.

Analytical Data:

NMR($^1$H, 360 MHz, CDCl$_3$): 1.02(t: J=7.5, 3H); 1.77 (sext: J=7.5, 2H); 2.52(t: J=7.5, 2H); 5.01(split s, 1H); 5.47(split s, 1H); 7.28–7.49(m, 5H).

NMR($^{13}$C, 90.5 MHz, CDCl$_3$): 18.4(t); 36.2(t); 102.0(t); 124.9(d, 2C); 128.5(d, 2C); 128.9(d); 134.5(s); 153.0(s); 171.8(s).

MS: 190(M+, 23); 162(40); 120(100); 105(35); 91(15), 77(22); 71(73); 43(60).

EXAMPLE 7

Preparation of a Perfuming Composition

A base perfuming composition of the hyacinth type was prepared by adding the following ingredients:

| Ingredients | Parts by weight |
| --- | --- |
| Benzyl acetate | 70 |
| Cinnamic alcohol | 45 |
| 1%* Methyl alcohol | 25 |
| 10%* Methyl cyclopentylideneacetate[1)] | 3 |
| Cyclamen aldehyde | 7 |
| Eugenol | 20 |
| Galaxolide ®[2)] | 15 |
| Hedione ®[3)] | 7 |
| Methylisoeugenol | 3 |
| Phenethylol | 125 |
| 2-Phenoxy-ethanol | 157 |
| Rosinol[4)] | 3 |
| Amyl salicylate | 60 |
| 10%* Methyl salicylate | 3 |
| Scentenal ®[5)] | 3 |
| Veloutone | 4 |
| Total | 550 |

*in dipropyleneglycol
[1)]origin: Firmenich SA, Geneva, Switzerland
[2)]1,3,4,6,7,8-hexahydro-4,6,6,7,8,8-hexamethyl-cyclopenta-γ-2-benzopyrane; origin: International Flavours and Fragrances, USA
[3)]methyl dihydrojasmonate; origin: Firmenich SA, Geneva, Switzerland
[4)]2,2,2-trichloro-1-phenylethyl acetate; origin: Firmenich SA, Geneva, Switzerland
[5)]8(9)-methoxy-tricyclo[5.2.1.0.(2,6)]decane-3(4)-carbaldehyde; origin: Firmenich SA, Geneva, Switzerland The addition of 70 parts by weight of 1-phenylvinyl acetate at 10% in dipropylene glycol imparted to this base composition an interesting olfactory effect of the white flowers type, rending the odor notes of the composition more flowery, powerful, rosier and more natural than when lacking 1-phenylvinyl acetate.

The composition comprising 1-phenylvinyl acetate was further compared with the same base composition wherein indole at 10% in dipropyleneglycol had been added instead of 1-phenylvinyl acetate. The former composition was preferred by all the perfumers constituting a panel of 7 people, who described its odor as less animal, more white flowers and much more natural than that of the composition comprising indole.

EXAMPLE 8

Preparation of a Perfuming Composition

A base perfuming composition of the Sambac jasmine type was prepared by adding the following ingredients:

| Ingredients | Parts by weight |
| --- | --- |
| 10%* 3-Hexenyl acetate | 5 |
| Benzyl acetate | 250 |
| 10%* Cinnamyl acetate | 10 |
| 1%* Cis-3-hexenol acetate | 25 |
| 10%* Geranyl acetate | 25 |
| Phenylethyl acetate | 10 |
| 50%* Cinnamic alcohol | 10 |
| Methyl anthranilate | 180 |
| Cis-hexyl benzoate | 200 |
| Fenchyl benzoate | 15 |
| Methyl benzoate | 5 |
| 10%* Ethyl benzoate | 10 |
| 10%* Cis-3-hexenol butyrate | 20 |
| 10%* Cis-3-hexenol caproate | 5 |
| 10%* Cis-3-hexenol | 5 |
| 10%* Cis-jasmone | 15 |
| 10%* Cis-ocimene | 5 |
| Farnesene | 300 |
| Geraniol | 5 |
| Hedione ®[1)] | 105 |
| 10%* Cis-3-hexenol isobutyrate | 20 |
| 10%* Isojasmone | 10 |
| Linalol | 70 |
| Methyl linoleate[2)] | 100 |
| 10%* Cis-3-hexenol methylbutyrate | 5 |
| 10%* Methylhexenone | 5 |
| 1%* Paracresol | 20 |
| Phenethylol | 10 |
| Benzyl salicylate | 10 |
| Methyl salicylate | 5 |
| 10%* Ethyl salicylate | 5 |
| 10%* Cis-3-hexenol 2-methyl-2-butenoate | 5 |
| 10%* Z-2-hexenal | 30 |
| Total | 1500 |

*in dipropyleneglycol
[1)]methyl dihydrojasmonate; origin: Firmenich SA, Geneva, Switzerland
[2)]methyl (Z,Z)-9,12-octadienoate; origin: Firmenich SA, Geneva, Switzerland When 100 parts by weight of 1-phenylvinyl acetate were added to this jasmine base composition, the latter acquired the natural, very indolic connotation of jasmine, its odor being very close to that of the base composition wherein the same quantity of indole had been added. The odor of the new composition comprising 1-phenylvinyl acetate was slightly more floral-fruity than that of the composition comprising indole, less naphthalenic and above all its color remained straw yellow, even after 3 months, while the color of the same base composition where indole was added, became dark red after a few days.

What is claimed is:

1. A method to impart, enhance or modify the odor properties of a perfuming composition or a perfumed product, which method comprises adding to said composition or product a compound of formula

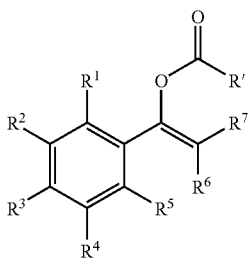

(I)

wherein the symbol R' represents a linear or branched, unsaturated or saturated hydrocarbon group having from 1 to 5 carbon atoms; $R^1$, $R^2$, $R^3$, $R^4$ and $R^5$ represent, independently of each other, a hydrogen atom, a methyl, an ethyl or a methoxy group; $R^6$ and $R^7$ represent, independently of each other, a hydrogen atom, a methyl, ethyl, n-propyl or iso-propyl group; and $R^5$ and $R^6$, when taken together with the carbon atoms to which they are bound, may form a six-membered ring; and wherein the compound imparts odor notes of the floral or indolic type and of substantial volume and of a power easily comparable to that of indole.

2. Method according to claim 1, wherein, in formula (I), $R^1$, $R^2$, $R^3$, $R^4$, $R^5$, $R^6$ and $R^7$ all represent hydrogen atoms.

3. Method according to claim 2, wherein 1-phenylvinyl acetate is added to the composition or product.

4. Method according to claim 3, wherein 1-phenylvinyl acetate imparts an indolic odor note to the composition or product.

5. Method according to claim 2, wherein 1-phenylethenyl propanoate is added to the composition or product.

6. Perfuming composition or perfumed product containing as active ingredient, together with solvents or adjuvants currently used for the preparation of a perfume formulation, a compound of formula (I) as defined in claim 1.

7. Perfuming composition or perfumed product according to claim 6, containing 1-phenylvinyl acetate as active ingredient.

8. Perfumed product according to claim 6, in the form of a perfume or cologne, a soap, a shower or bath gel, a shampoo or another hair-care product, a cosmetic preparation, a body deodorant or an air-freshener, a detergent or fabric softener or a cleaning product.

9. A compound of formula

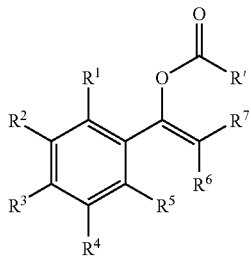

(I)

wherein the symbol R' represents a linear or branched, unsaturated or saturated hydrocarbon group having from 1 to 5 carbon atoms; $R^1$, $R^2$, $R^3$, $R^4$ and $R^5$ represent, independently of each other, a hydrogen atom, a methyl, an ethyl or a methoxy group ; $R^6$ and $R^7$ represent, independently of each other, a hydrogen atom, a methyl, ethyl, n-propyl or iso-propyl group; and wherein $R^5$ and $R^6$, when taken together with the carbon atoms to which they are bound, may form a six-membered ring; provided that 1-phenylvinyl acetate, 1-(2,6-diethylphenyl)vinyl acetate, 1-(2-methylphenyl)vinyl acetate, 1-(2,4,6-trimethylphenyl)vinyl acetate, 1-(4-methylphenyl) vinyl acetate, 1-phenylvinyl 2-methyl 2-propenoate, 1-phenylvinyl 2-butenoate, 1-phenylvinyl butanoate, 1-phenylvinyl propanoate, 1-phenylvinyl 2,2-dimethyl propanoate, 1-phenylvinyl pentanoate, 1-phenylvinyl 2-methyl propanoate and 1-(4-methoxyphenyl)vinyl acetate are excluded.

* * * * *